United States Patent [19]
Gow

[11] Patent Number: 5,888,246
[45] Date of Patent: Mar. 30, 1999

[54] MOTOR DRIVE SYSTEM AND LINKAGE FOR HAND PROSTHESIS

[75] Inventor: David James Gow, Edinburgh, Scotland

[73] Assignee: Royal Infirmary of Edinburgh NHS Trust, Edinburgh, Scotland

[21] Appl. No.: 702,605

[22] PCT Filed: Mar. 10, 1995

[86] PCT No.: PCT/GB95/00518

§ 371 Date: Sep. 6, 1996

§ 102(e) Date: Sep. 6, 1996

[87] PCT Pub. No.: WO95/24875

PCT Pub. Date: Sep. 21, 1995

[30] Foreign Application Priority Data

Mar. 12, 1994 [GB] United Kingdom .................. 9404830

[51] Int. Cl.⁶ ....................................................... A61F 2/54
[52] U.S. Cl. .............................................................. 623/64
[58] Field of Search .................................. 623/64, 63, 57, 623/58; 414/4; 901/38; 601/5, 33, 40; 602/22

[56] References Cited

U.S. PATENT DOCUMENTS

| | | |
|---|---|---|
| 3,509,583 | 5/1970 | Fraioli . |
| 3,683,423 | 8/1972 | Crapanzano . |
| 4,505,166 | 3/1985 | Tesar ........................................ 414/4 X |
| 4,623,354 | 11/1986 | Childress . |
| 4,792,338 | 12/1988 | Rennerfelt . |
| 4,923,477 | 5/1990 | Horvath . |

FOREIGN PATENT DOCUMENTS

| | | |
|---|---|---|
| 8801143 | 1/1991 | Czechoslovakia . |
| 330551 | 8/1989 | European Pat. Off. .................. 901/38 |
| 309367 | 11/1918 | Germany . |
| 2607499 | 1/1977 | Germany . |
| 1181863 | 9/1985 | U.S.S.R. .................................... 901/38 |
| 1510298 | 5/1978 | United Kingdom . |
| 1571140 | 7/1980 | United Kingdom . |

*Primary Examiner*—David H. Willse
*Attorney, Agent, or Firm*—Young & Basile, P.C.

[57] ABSTRACT

A motor drive system and linkage arrangement for a hand prosthesis, wherein the prosthesis has at least one finger member extending generally tangentially with respect to a worm gear wheel secured to the prosthesis and driven by a drive motor and a worm gear located longitudinally within the finger to engage the teeth of the tangential worm gear wheel. When the drive motor runs the worm gear, the finger moves around the worm gear wheel toward or away from another finger member and/or a natural finger to open and close the prosthesis hand's grip. In an alternate embodiment, the drive motor and worm gear arrangement contained in one finger is connected by a linkage to the root portion of at least one other motorless finger mounted for pivotal movement on the prosthetic hand.

8 Claims, 3 Drawing Sheets

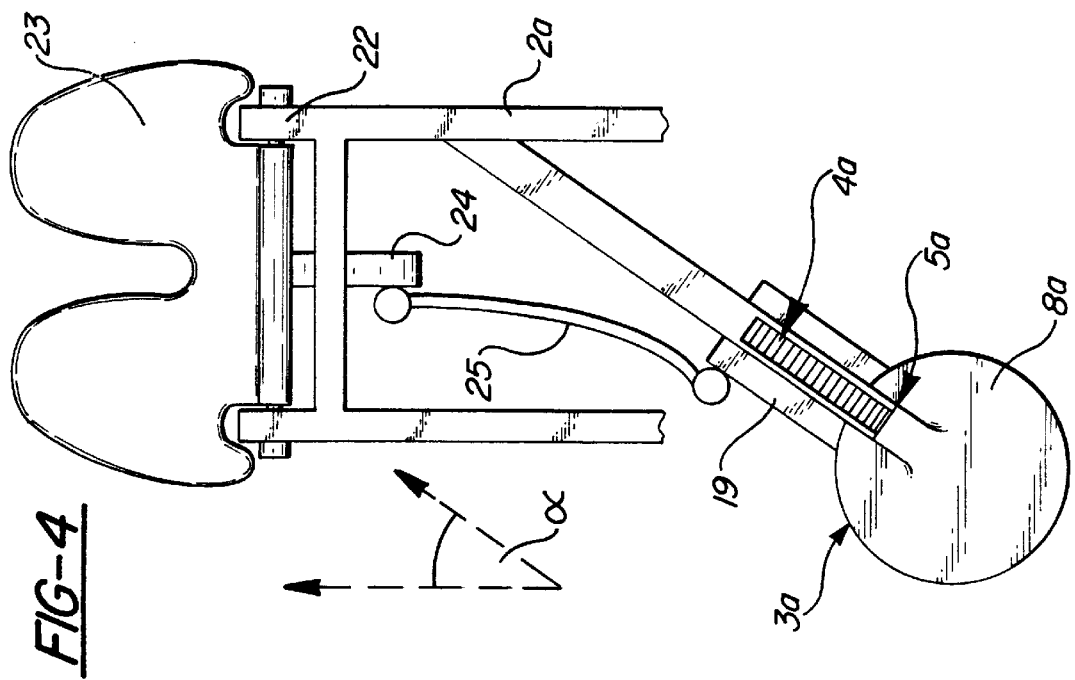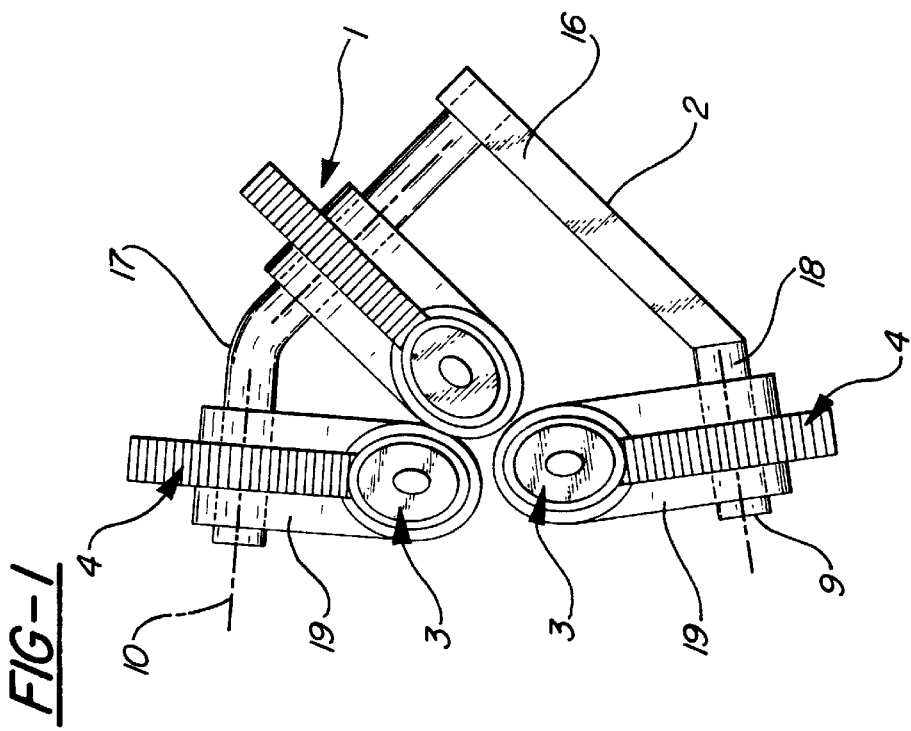

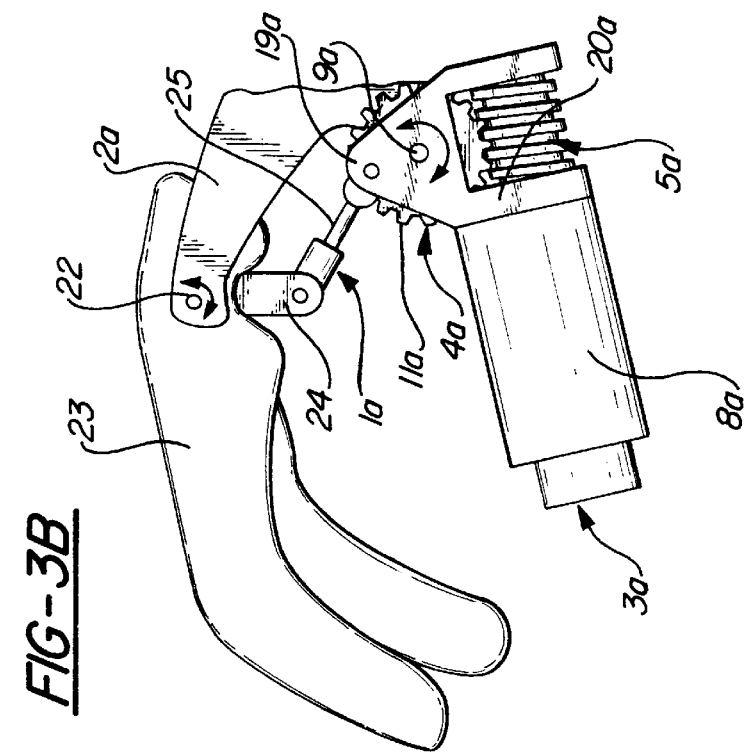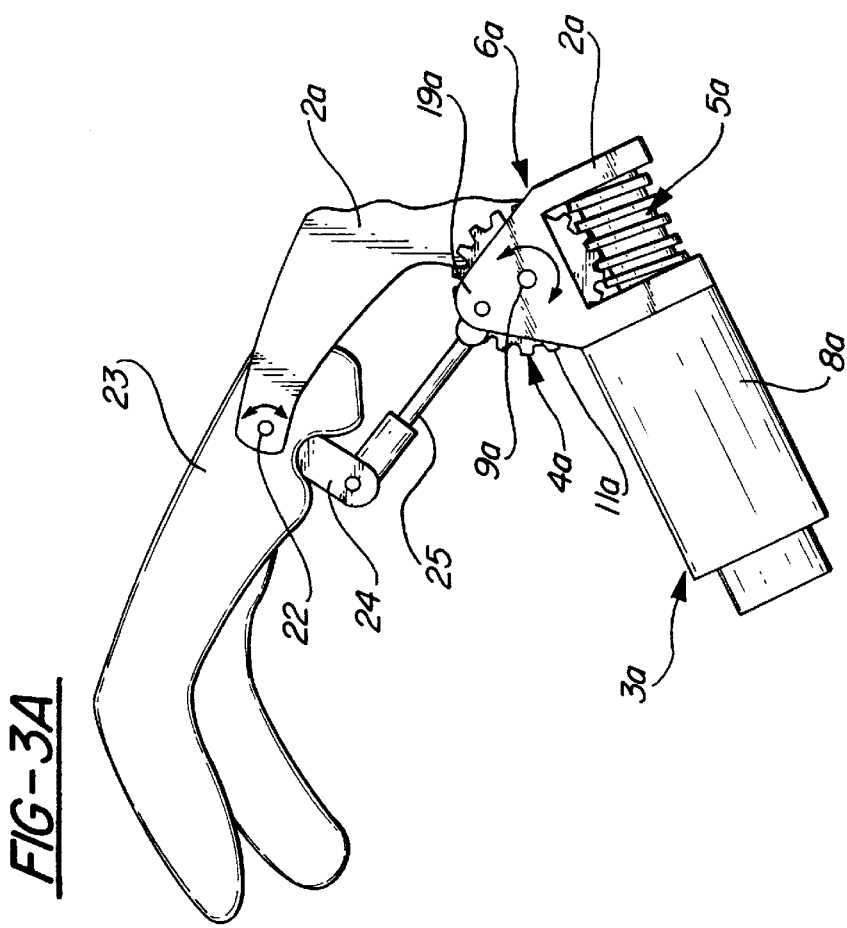

MOTOR DRIVE SYSTEM AND LINKAGE FOR HAND PROSTHESIS

FIELD OF THE INVENTION

The present invention relates to hand prostheses and in particular to such prostheses with movable gripping fingers.

BACKGROUND OF THE INVENTION

The design of such hand prostheses presents formidable problems in achieving gripping light enough to handle fragile objects and strong enough to provide a secure grip to objects where it is desired to apply substantial forces. These problems are further compounded by the limited spaced available, especially within the fingers themselves, and where it is required to provide for independent movement of different fingers to a greater or lesser extent, and/or varying the rate of movement of individual fingers.

A particular problem arises with the fitting of hand prostheses in patients with relatively long hand stumps. Conventional electrical hand prostheses use an electric motor mounted in the body structure of the hand itself. Some versions have the motor mounted axially parallel to the long axis of the arm and others have the motor at 90 degrees to this axis. A variety of transmission systems are used to link motor and fingers e.g. lead screw and nut, or bevel and spur gears. Without exception these types of hand prosthesis require precise alignment between motor and transmission system. This is usually achieved by locating all the parts within a hand body consisting of an investment casting or other moulded structure. Such an arrangement is relatively cumbersome and the motor cannot be readily accommodated within the limited space available in the main body of the prosthesis attached to the patient's hand stump. Another disadvantage is that patients with some residual digits cannot have any functional restoration at all because of the space constraints. The operational characteristics of such devices also tend to be restricted e.g. allowing only a single gripping pattern to be employed.

SUMMARY OF THE INVENTION

It is an object of the present invention to avoid or minimise one or more of the above disadvantages.

The present invention provides a prosthesis for providing at least one mechanically operable finger member, said prosthesis having at least one said finger member extending generally tangentially with respect to a fixed worm gear wheel means on a support body of said prosthesis and mounted for rotation about the worm gear wheel spindle, said finger member having a drive motor with a worm extending generally longitudinally of the finger member and in engagement with the gear teeth of said worm gear wheel so that when said drive motor is operated, in use of the prosthesis, said finger member moves around said worm gear wheel towards or away from another finger member and/or a natural finger for closing and opening of a hand grip.

Thus the hand prosthesis of the present invention uses a particularly compact form of finger drive which also can allow improved operational flexibility.

As used herein the expression "finger member" includes a "thumb member". Whilst it is possible to provide a useful hand grip defined by just one movable finger member and one fixed member, it is generally preferred to have a hand prosthesis with a plurality of movable finger members, most preferably with control means formed and arranged so as to permit more or less, independence of movement of the finger members or groups of finger members, e.g. to allow higher speed lower torque movement of a "thumb" finger member, and slower speed higher torque movement of the other finger(s), and/or to permit the provision of different gripping patterns with different combinations of individual/group finger movement characteristics.

Conveniently a root portion of said at least one said finger member provided with a drive motor is connected by a linkage means to the root portion of at least one other (motor-less) finger member mounted for pivotal movement on said support body, said linkage means being formed and arranged for transmitting drive to said other finger member so as to pivotally move said other finger member towards or away from said at least one finger member provided with a drive motor during direct movement thereof by the drive motor for closing and opening of a hand grip.

Whilst this kind of arrangement may have less power and operational flexibility than other forms of the invention in which separate motors are used for different fingers, it does have the advantage of requiring fewer motors and less power consumption thereby providing a more economical solution.

Various suitable motors having a relatively high power-to-weight ratio are known in the art including permanent magnet DC motors which have a substantially linear relation between torque and drive current over a reasonably wide range which facilitates control of the driving of the finger member. Particularly suitable motors are available from Minimotor SA of Switzerland, especially their motors which have a diameter of around 8 to 17 mm. A further advantage of this type of motor is the availability of a modular gearbox system coupled to the output shaft of the motor which allows different torque-output drive speed ratios to be selected simply by choosing from a range of gearboxes with different ratios. This has the advantage of facilitating the provision, in a prosthesis, of different gripping patterns by simply using different gearboxes in different finger members.

In general it is preferred to have a faster moving lower torque thumb finger member with slower moving higher torque other finger members as this simplifies the provision of a cosmetically acceptable sheathing or cladding of the mechanical components of the prosthesis due to the reduced range of movement of the other finger members.

The compact form of drive motor and mounting thereof substantially within the finger member being driven, particularly when said drive motor is inside a thumb finger member, allows for a reduction in finger size and hence a lighter construction, which is particularly desirable in application of the prosthesis to children. Moreover the compactness allows fitting to longer stumps which include a mobile wrist without any loss of wrist mobility and without making the hand appear too long.

Further preferred features and advantages of the invention will appear from the following detailed description given by way of example of some preferred embodiments illustrated with reference to the accompanying drawings in which:

BRIEF DESCRIPTION OF THE DRAWINGS

FIG. 1 is an end view of the principal components of the operating mechanism of a hand prosthesis of the invention;

FIGS. 3 (*a*) and (*b*) are perspective views of a second embodiment of hand prosthesis of the invention; and FIG. 4 is a rear view of the hand prosthesis shown in FIGS. 3 (*a*) and (*b*).

DETAILED DESCRIPTION OF THE ILLUSTRATED EMBODIMENTS

Figure 2:
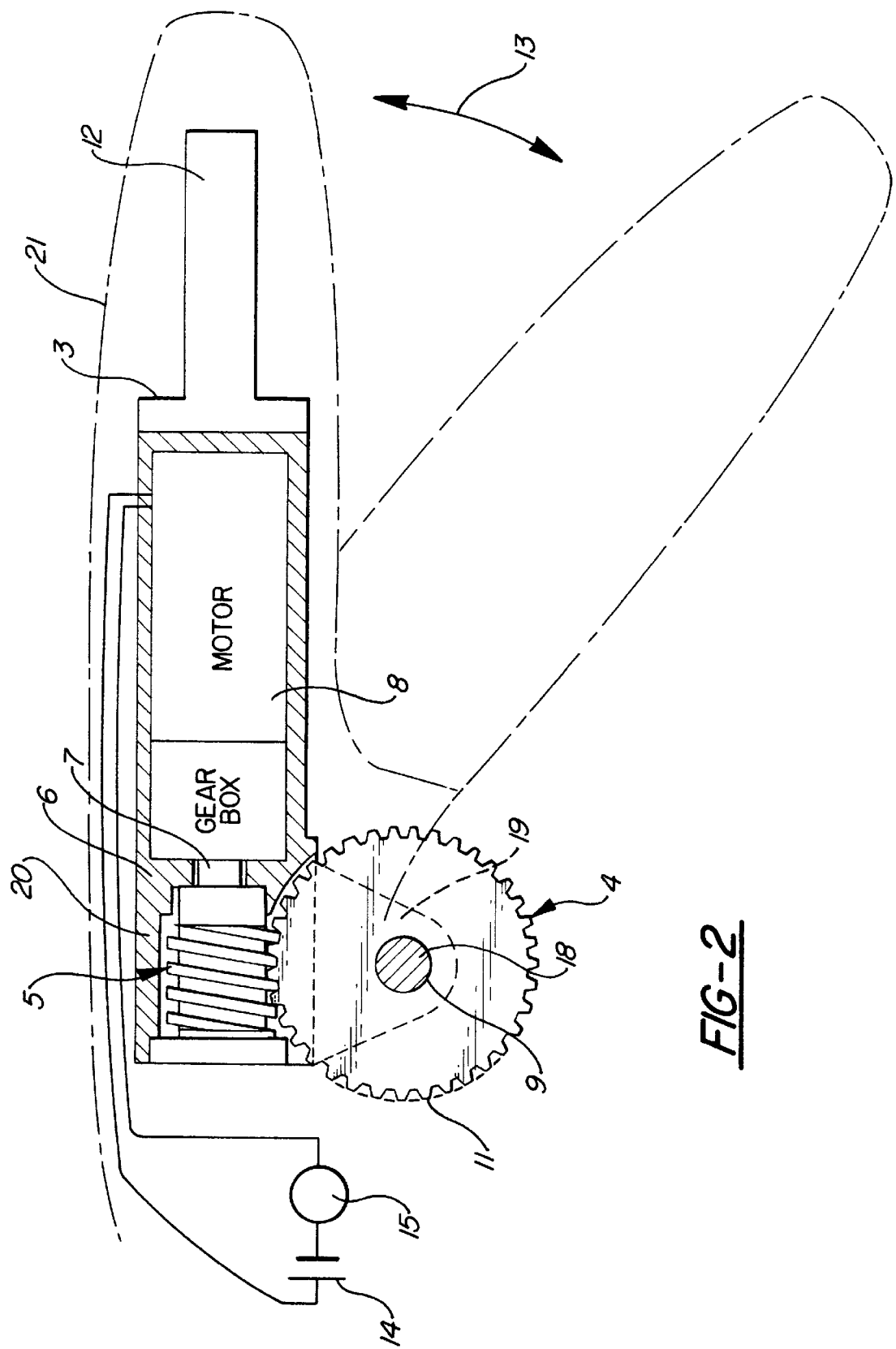
FIG. 2 is a partly cut-away view of one finger member of hand prosthesis using the mechanism of FIG. 1.

FIG. 1 shows the principal components of the operating mechanism 1 of a hand prosthesis having a main body 2 which is securely fixed in use to a patient's hand stump (not shown) in generally known manner, and a plurality of finger members 3. The main body 2 has mounted thereon a plurality of fixed worm wheels 4 for engagement, each with a worm 5 mounted in the base 6 of a respective finger member 3 to extend generally tangentially of the fixed worm wheel 4. The worm 5 is mounted on the drive shaft 7 of a gearbox and drive motor combination 8 extending longitudinally of the finger member 3. The finger member 3 is pivotally connected 9 to the main body 2 for pivoting about the axis 10 of the fixed worm wheel 4 so that when the motor 8 is actuated to drive the worm 5, the worm travels around the circumference 11 of the fixed worm wheel 4. At the same time the distal end 12 of the finger member 3 describes an arc indicated by the arrows 13 for opening and closing of a hand grip.

The motor 8 is powered by small rechargeable Nickel Cadmium batteries 14 (shown schematically) which may be remotely mounted e.g. in the 4th and 5th fingers (not shown) of the prosthesis or in any suitable space between the stump (not shown) and the prosthesis.

The motor 8 is controlled by means of switches 15 actuated by either residual digit movement or by wrist motion. Two switches may be used to control both directions of rotation or alternatively one switch may, by being interfaced through suitable electronic circuitry, be used to control both directions in a sequential or toggled manner. In addition to switches, pressure signals derived from force sensitive resistor material or signals derived from the electromyographic activity of residual muscle actions, may be used as control signals.

The main body 2 of the prosthesis itself may conveniently be in the form of a simple bar 16 with finger and thumb spigots 17, 18 extending therefrom. The pivotal mounting of the finger members 3 is effected via lugs 19 which depend from a generally tubular housing 20 in which are mounted the motor 8 and worm 5.

The components 2 of the prosthesis operating mechanism 1 can be clad in an overlay 21 of silicone rubber or the like to provide a more aesthetically acceptable appearance as similar as practicable to a normal hand appearance, in generally known manner.

FIGS. 3 (a) & (b) and FIG. 4 shows a second embodiment of hand prosthesis and will be described with reference to the embodiment shown in FIGS. 1 and 2 and indicated by like reference indicia with suffix 'a' added. The operating mechanism 1a of a hand prosthesis has a main body 2a (only partially shown) which is securely fixed in use to a patient's hand stump in generally known manner. The main body 2a has mounted thereon a single fixed worm wheel 4a for engagement with a worm 5a mounted in the base 6a of a thumb finger member 3a to extend generally tangentially of the fixed worm wheel 4a. The worm is mounted on the drive shaft of a gearbox and drive motor combination 8a.

The thumb finger member 3a is pivotally connected 9a to the main body 2a for pivoting about the axis of the fixed worm wheel 4a so that when the motor 8a is actuated to drive the worm 5a, the worm travels around the circumference 11a of the fixed worm wheel 4a. The main body 2a has pivotally mounted 22 thereon also a pair of finger members 23. The finger members 23 have an inwardly depending lever 24 pivotally connected by a generally arcuate or cranked linkage member 25 to a lug 19a which extends from the housing 20a in which is mounted the motor 8a and the worm 5a. As may be seen from FIG. 4 the pivotal plane of the thumb finger member 3a is inclined (generally by an inclined angle α of around 55° to 60°) relative to that of the finger members 23 to provide a more natural arrangement.

It will be seen from FIGS. 3 (a) and (b) that when the motor 8a is actuated to drive the worm 5a, the worm travels around the circumference 11a of the fixed worm wheel whilst driving the linkage member 25 against the inwardly depending lever 24 on the finger members 23 so as to transmit drive thereto so as to pivotally move the finger members 23 towards or away from the thumb finger member 3a for closing (FIG. 3 (b)) and opening (FIG. 3 (a)) of a hand grip.

As with the first embodiment described hereinbefore the components of the second embodiment of prosthesis can be clad in an overlay of silicone rubber or the like to provide a more aesthetically acceptable appearance, in generally known manner.

The compact form of finger drive and mounting thereof substantially within the finger being driven thereby, as well as the essential neutrality i.e. non-handedness of its configuration, allow an essentially modular approach to the construction of electrically operated hand prostheses. This in turn leads to a number of advantages including one or more of reduced stockholding requirements as various different prostheses, including left and right handed ones and ones with different numbers of mechanical fingers may be readily assembled from a small number of common components. In addition different grip patterns can be readily achieved by use of suitable controls with the independent finger drives, with the further advantage that there is no need to compromise between grip force and speed of operation or movement.

The modularity and compactness of the units also allows individual finger prostheses to be used e.g. in the case of congenital deformities of the type where one or more fingers, especially the middle fingers which are important to effective prehension, are missing.

Accordingly, I claim:

1. A prosthesis having at least one mechanically operable finger member, the finger member extending generally tangentially with respect to a fixed worm gear wheel on a support body of the prosthesis and mounted for rotation about a worm gear wheel spindle, the finger member having a drive motor with a worm extending generally along a longitudinal axis of the finger member and in engagement with gear teeth on the worm gear wheel so that when the drive motor is operated, in use of the prosthesis, the finger member moves around the worm gear wheel towards or away from another finger member and/or a natural finger for closing and opening of a hand grip.

2. A prosthesis according to claim 1 wherein a root portion of at least one finger member is provided with a drive motor connected by a linkage means to a root portion of at least one other finger member mounted for pivotal movement on the support body, the linkage means being formed and arranged for transmitting drive to the other finger member so as to pivotally move the other finger member towards or away from the at least one finger member provided with a drive motor during direct movement thereof by the drive motor for closing and opening of a hand grip.

3. A prosthesis according to claim 2 wherein the drive motor is a permanent magnet D.C. motor having a substantially linear relation between torque and drive current.

4. A prosthesis according to claim 3 wherein the drive motor is coupled to a gearbox system whereby in use different torque-output drive speed ratios may be selected from a range of gearboxes with different ratios.

5. A prosthesis according to claim 4 having a plurality of finger members and provided with control means formed and arranged so as to permit independence of movement of at least one of the finger members with respect to other of the finger members.

6. A prosthesis according to claim 5 wherein the plurality of finger members includes a single thumb finger member having a drive motor with high speed, low torque characteristics and at least one other finger member having a drive motor with low speed, high torque characteristics.

7. A prosthesis according to claim 6 clad with an overlay of aesthetically acceptable material having an appearance generally similar to a normal hand appearance.

8. A prosthesis according to claim 5, wherein the control means is formed and arranged so as to permit independence of movement of a first group of the finger members with respect to a second group of the finger members.

\* \* \* \* \*